United States Patent [19]

Orthuber et al.

[11] Patent Number: 4,656,860

[45] Date of Patent: Apr. 14, 1987

[54] DENTAL APPARATUS FOR BENDING AND TWISTING WIRE PIECES

[76] Inventors: Wolfgang Orthuber, Arbeostrasse 3, 8358 Vilshofen; Helge Fischer-Brandies, Walterstrasse 22/V, 8000 Munich, both of Fed. Rep. of Germany

[21] Appl. No.: 717,031

[22] Filed: Mar. 28, 1985

[30] Foreign Application Priority Data

Apr. 19, 1984 [DE] Fed. Rep. of Germany ....... 3415006

[51] Int. Cl.$^4$ .............................................. B21D 11/14
[52] U.S. Cl. ........................................ 72/299; 72/307; 72/7; 140/149; 433/3
[58] Field of Search ...................... 72/307, 299, 371, 7; 140/149; 364/413; 433/2, 3

[56] References Cited

U.S. PATENT DOCUMENTS

| | | | |
|---|---|---|---|
| 3,373,587 | 3/1968 | Shubin et al. | 72/307 |
| 3,563,283 | 2/1971 | Tufektshiev | 72/307 |
| 3,823,749 | 7/1974 | Ritter et al. | 72/307 |
| 4,131,003 | 12/1978 | Foster et al. | 72/7 |
| 4,161,110 | 7/1979 | Ritter et al. | 72/7 |
| 4,479,182 | 10/1984 | Beier | 364/413 |

Primary Examiner—Daniel C. Crane
Attorney, Agent, or Firm—Laurence R. Brown

[57] ABSTRACT

In dental treatment for fitting a wire piece onto the teeth and/or jaw, a patient is subjected to repeated bending and in some cases twisting of the wire and some arrangement for completing the treatment, with whose help the bending and twisting process takes place automatically by machinery. Accordingly, next the data about the shape of the teeth and/or jaw is ascertained and put into an electronic computer, where this data is converted into control data. The wire piece will then be put into a bending machine with separately controlled stepping drives for advancing the wire, twisting and bending, whose drive through the command of the computer will automatically be controlled. The bending machine comprises essentially an advancing means, a torsion work piece of two grippers relatively rotatable with each other and a bending work piece with a moving bending edge substantially perpendicular to the wire axis. The advancing means, twisting work piece and bending work piece are in each case coupled to drive means.

3 Claims, 7 Drawing Figures

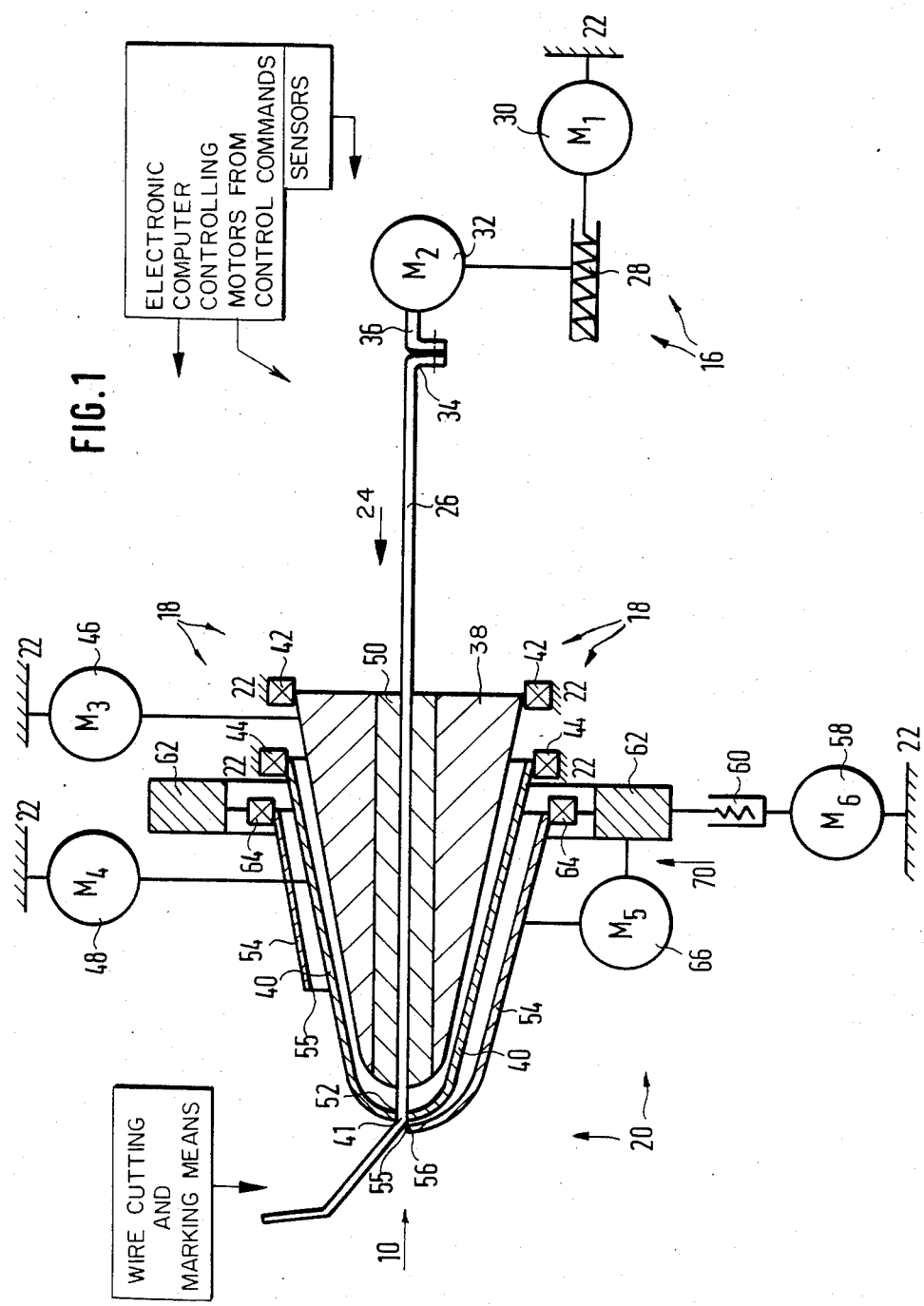

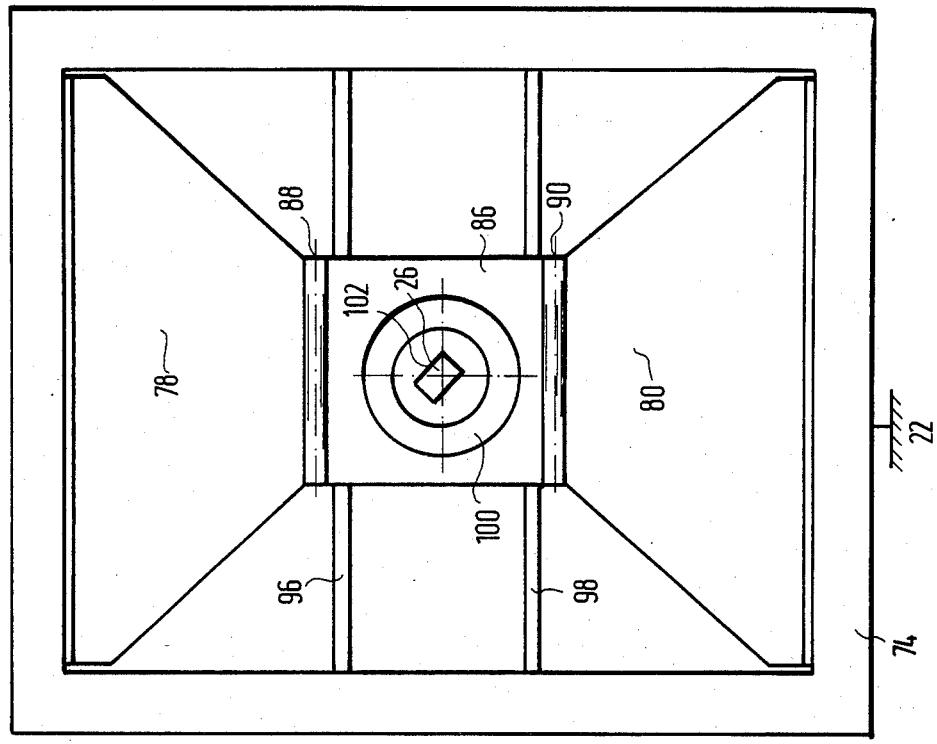
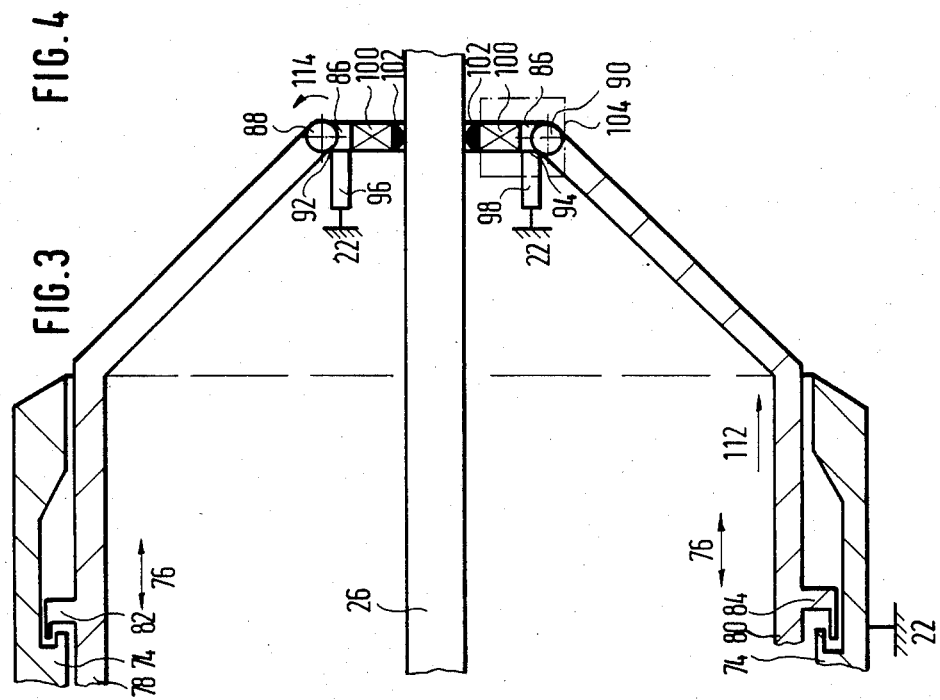

DENTAL APPARATUS FOR BENDING AND TWISTING WIRE PIECES

FIELD OF THE INVENTION

This invention relates to dental methods for fitting wire pieces to the teeth and/or jaw of a patient by means of several bends and in some cases twisting of the wire, as well as equipment for practicing these methods.

BACKGROUND ART

In dental medicine, especially jaw orthopedics, (orthodontics) it is often necessary outside the mouth by fixed apparatus from straight wire pieces by several bends and in some additional twisting to fit the teeth and/or jaw shape of individual patients. This bending and twisting equipment is manually fed, which not only is time consuming but also demands great skill. As a result in many cases the desired production of the bending by this manual work process is not generally achieved.

An object of this invention is to provide a method and apparatus with which it is possible to fit necessary bends and twists quickly, exactly and effortlessly and furthermore with exact reproducibility. The solution of these problems and for the equipment are set forth in the claims.

DISCLOSURE OF THE INVENTION

With the invention it is also possible to mechanize the desired process, especially by means of a bending machine whose work process, namely advancing, twisting and bending wire, is controlled by an electronic computer. Orthopedics provide first in the computer the desired data for the shape of the wire piece, whereby a straight wire piece fed into the bending machine, will be automatically controlled by the computer for the entire bending and twisting process. The wire piece thus is fed stepwise through the machine and between the advancing steps is twisted and/or bent. It is understood that compared with manual work, the speed and accuracy is substantially increased. Also, the process is substantially less trouble since the desired data is simply stored in the computer. Finally, an exact reproduction can result in a simple manner from the data stored in the computer. Accordingly, it is possible by suitable programming of the computer, to feed in definite time intervals at least partly automatically while making the desired changes with the present knowledge in the art.

Preferred embodiments of the bending machine of this invention are described in the appended claims.

BRIEF DESCRIPTION OF THE DRAWINGS

The embodiments of the bending machine of this invention are set forth in the drawing, where it is shown:

FIG. 1 is a schematic diagram in cross section, with the bending plane shown, of a first embodiment of the bending machine, FIG. 3 is a view as in FIG. 1 of a second embodiment of the bending machine, FIG. 4 is a front view of the machine of FIG. 3 in the direction of the arrow 112.

THE PREFERRED EMBODIMENTS

Figure 5:
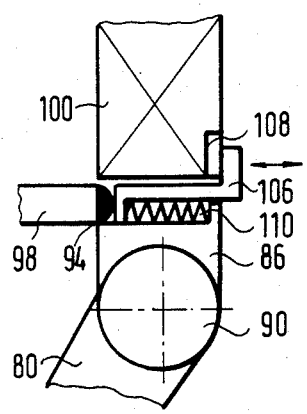
FIG. 5 is a locking mechanism of the rotating bearing of the bending machine of FIG. 3.

The bending machine shown schematically in FIG. 1 can functionally be separated into three main parts, namely: advancing apparatus 16, torsion apparatus 18 and bending apparatus 20.

In this respect the main parts 16, 18 and 20 are arranged and anchored in the partly shown housing 22. The wire 26 is arranged to run through the machine in the direction of the arrow 24 from the advancing apparatus 16 through the torsion apparatus 18 and then through the bending apparatus 20. As a consequence these three main elements 16, 18 and 20 become a single unit.

The support equipment 16 comprises a screw threaded spindle 28, which is driven by an anchored advancing motor (stepping motor) 30. The threaded spindle 28 is fixed by a sliding carriage (not shown in the drawing) to motor 32 which causes the turning of the wire 26 and therefore is shown alongside the wire turning motor 32. The wire 26 is fastened onto the drive shaft 36 of the wire turning motor 32 at 34 to turn without slippage. As a result, if the wire in its end portion breaks off, so that its direction becomes stationary, then a definite turning about the axis of the wire is possible, as when the wire is round.

The torsion apparatus 18 essentially comprises a bowl like torsion tool 38 and a rotatable lamination 40 with a gate 41 for passing the wire. Their shape about their axis of symmetry corresponds to a rotating parabola such that the axis of symmetry is coincident with the wire axis. Tool 38 and lamination 40 are rotatable about the wire axis in the bearings 42 and 44 fastened to the housing, so that the rotation of the tool 38 by a motor 46, hereinafter shown as torsion motor 46, causes the rotation of the lamination 40 there against by means of a motor 48. The torsion tool 38 has a thick wire adjoining surface 50 through which the wire 26 in its advancing direction 24 passes. However, at the same time, when the wire is not round, it is secured against a twisting about its axis by rotation of the torsion tool 38. The rotating lamination 40 has a small wire contacting surface 52 through which the wire axially passes but unround wire is retained against radial rotation. Thereby the wire 26 passes freely between the torsion tool 38 and the rotating lamination 40.

Figure 2:
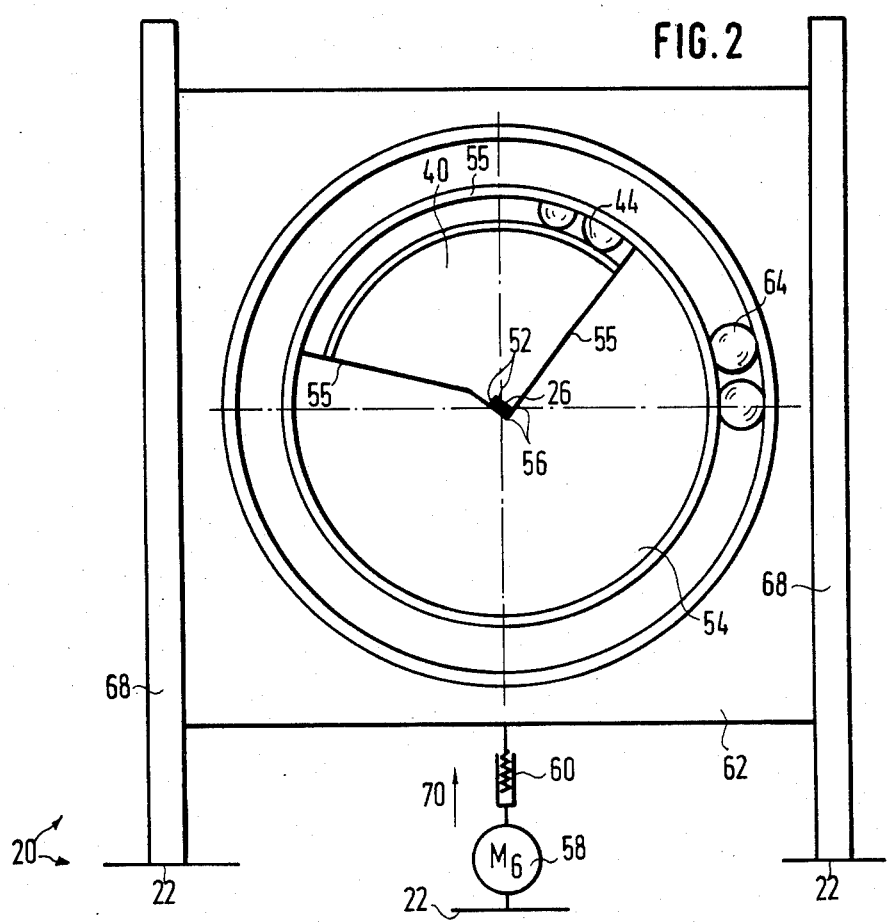
FIG. 2 is a front view of the machine of FIG. 1 in the direction of arrow 10.

The bending apparatus 20 comprises a bending lamination 54 and a rotatable lamination, wherein the rotating lamination is formed by the rotating lamination 40 of the torsion apparatus 18. The rotating lamination 40 also functions as well as also the bending apparatus 20 is formed as a part of the torsion apparatus 18. The lamination like bending tool 54 is similarly formed as the rotatable lamination 40, presenting likewise a window 55 through which the wire passes, which as best shown in FIG. 2, presents a notch above the wire. Through this form and equipment of the window 55 the bending tool 54 is caused to border the underside of the wire 26, namely with the bending edge 56 (underedge of the window 55). The wire towards the top, however, has a freedom of movement. The drive of the bending apparatus results from a bending motor 58 fastened to the housing, and by means of a threaded spindle 60, which is affixed to a drive member 62. By this drive member 62 the bending lamination 54 is turnable in a bearing 64 about the wire axis. The rotation results from motor 66 mounted on the drive member 62, so that it is called the lamination driving motor 66. The driving member 62 is mounted to vertically slide on a carriage 68 of housing 22.

The functioning of the bending machine will next be described for the case of a round wire 26, but also a wire which must be simply bent but not twisted.

The round wire 26 lying in the machine is by means of the screw threaded spindle 28 and the forward movement motor 30 by way of wire turning motor 32 moved stepwise in the direction of arrow 24 and thus passes through the wire surrounding bearing 50, and through torsion tool 38 and passage 52 of the rotatable lamination 40, which borders on it on all sides and leads towards the bending edge 56. Each time then, when an advancing step of the wire 26 is taken between the surrounding surface 52 of the rotatable lamination 40 and the bending edge 56 for bending, the bending motor 58 pushes by means of the screw threaded spindle 60 of the drive member 62 and thus the bending lamination 54 in the direction of the arrow 70. The wire 26 is thereby by means of this motion (not effected by surrounding surface 52) with the bending edge 56 is upwardly bent, whereby the amount of the bending is determined by the movement of the bending lamination 54 and therewith by the bending motor 58. The bending follows in an exactly defined bending plane relative to the machine, in the foregoing case in the plane of the drawing in FIG. 1. This is done whatever the bending direction of the wire to be chosen, because of the rotation of the wire 26 about its axis. This rotating arrangement of the wire 26 about its axis clearly determines the bending direction. The turning can be initiated for each bending event by means of the wire turning motor 32.

The advancing apparatus (16, 116), bending apparatus (20, 120) and twisting apparatus (18, 118) are each controlled by electronic commands to controlled drive motors (30, 46, 58) so that the twisting apparatus (18, 118) by means of two relatively opposing rotatable grippers (30, 40, 124) having associated drive means (46) grip two places axially spaced from one another on the wire 26 and the bending apparatus (20, 120) comprises a movable bending edge (56) movable substantially perpendicular to the axis of the wire by means of an associated drive means (58).

Hereafter the functioning with a squared or unround wire is discussed, which in addition to the bending will be subjected to torsion.

The advancing of the squared wire proceeds as in the case of round wire. The surrounding surface 50 of the torsion tools 38 and 52 from the rotatable lamination 40 however with a squared wire has in addition to the advancement of the wire, the task of twisting it. Soon after the wire 26 exits from both surfaces 50 and 52, it can be twisted as a consequence of a rotation of both surfaces 50 and 52 relative to each other. Precisely stated, the torsion motor 46 turns the torsion tool 38, while the wire turning motor 48 turns the rotating lamination 40 against a torsion stop. The wire turning motor 32 as a result of the squared wire notwithstanding, should however provide the advantage that it understates the rotation of the torsion tool 38 and thereby the function of a rotating lamination, so that a tension free advancing of the wire 26 may be realized. The bending of the wire follows essentially as in the case of the round wire however, to yield two peculiarities. While with round wire the bending direction by the wire turning motor 36 and its shaft 36 is fixed, there results with the rotation of the squared wire, twisting the wire by means of wire turning motor 48 and the rotating lamination 40, which during the foregoing torsion motion has a detaining function.

Furthermore it is of importance that the bending lamination motor 66 only has the function that the bending lamination 54 for each bending apparatus so twists that its bending edge 56 runs parallel to the under surface of the wire, the wire underside also at the same time lying on the bending edge. This prevents the wire during the bending from being overridden to thus become uncontrollably defective. From FIG. 2 it is seen that this rotation from the position of the squared wire is dependent on the angular position of the rotating lamination 40. In each case it is assured through this precaution that in the case of a twisted squared wire, for example a wire with a right angular cross section, that the direction of bending is exactly defined.

The discussed torsion and bending action repeats itself often enough until all the desired twisting and bending is accomplished.

The number of twisting and bending actions, their place, their direction and their amount are controlled by the separate regulating motors 30, 32, 46, 48, 58 and 66. This exemplary complicated control can however, in a simple manner be attained, such that an electronic computer serves as the control element, which is supplied with a desired program. The operator then only has to put the desired program into the computer to control the motor by the computer so that the wire entering into the bending machine is automatically twisted and bent in the desired manner. This means however, that each time all parameters of the torsion and bending pertaining to numbers, place, amount and direction can be varied independently from each other. By combination of more small bends it is also possible to attain bends of greater radius. The same goes for torsion. The single limitation with reference to the bending resides in the possibility that a repeatedly bent wire can collide with the housing of the bending machine. To overcome this defect of the embodiment of FIG. 1, a newer version of the machine may be desired without the bending edge 56, in order that the mentioned risk is substantially lessened and the possibility of bending a much larger wire is created. In this way the shaping by the machine is brought to a higher reliability. Furthermore, it is possible that the control program be so fashioned that a possible striking of the wire at proper time through programmed adjusting bends will be prevented, in order that these adjusting bends after taking the wire out of the bending machine may be manually done. Clearly this procedure is only done in an extreme case. The motors may be electric, hydraulic or pneumatic, and it is possible only to have a single main drive, which then is connected over controllable couplings to drive the separate movement requirements.

FIG. 3 shows an embodiment of the bending machine with a modified bending apparatus 20. The same advancing apparatus 16 and torsion apparatus described may here be employed. The bending apparatus 20 according to FIG. 3, as also for FIG. 4, has a guidance cylinder 74 affixed to housing 22. This cylinder 74 moves in both horizontal directions of arrow 76 by means of a thrust motor (not shown) to move members 78 and 80, stabilized against vertical force by holding pins 82 and 84 preventing in the shown mating places the movement of the members 78 and 80 backward with the wire. Both members 78 and 80 hold between them a bending lamination 86 attached to two hinges 88 and 90. In the rest position they are at points 92 and 94 near two transverse rods 96 and 98 affixed to the housing 22. Confined during the bending in a resting place there against about the wire axis, rotatable member 100 holds the bending edge 102 twisting the wire 26 on all sides.

FIG. 5 shows in enlarged scale, what is in FIG. 3 shown as region 104, namely the construction of a possible latch mechanism for the member 100. In the shown resting position the transverse rod 98 at point 94 touches locking bolt 106 located at one of the bending laminations 86 so that it will release from the locking notch 108 a number of such notches 108 arranged about the circumference of the member. Without the said contact, the spiral spring 110 presses the locking bolt 106 into the locking notch 108 and thus arrests further rotation of the member 100.

The bending of the twisted and outwardly directed wire 26 takes place in this manner by pushing the sliding elements 80 in the direction of arrow 112, so that their neighboring elements 80 at the same time remain in the shown resting place. Thereby also the hinge 88 remains fixed in place, while the hinge 90 will be moved forward. The bending laminate 86, which is coupled to both hinges, rotates thereby in the direction of arrow 114 about the fixed hinge 88. The member 100 transmits the movement by means of its bending edge 102 to the wire 26 so that it will be bent upwardly. In this respect the transverse rod 98 which does not rest on the locking bolt at point 94 (FIG. 5), presses spiral spring 110 in one of the notches 108 of the member 100 and causes thereby the turning angle of the member in its place to effect the bending. The wire 26 has accordingly no possibility of twisting during the bending. The bending direction remains fixed in the embodiment of FIG. 3 and thus in a definite manner appreciably effected the previous twisting of the wire.

The advantage of the just described embodiment over that first described is namely that the motor 66 of FIG. 1 might slip, while this problem by the lockable element 100 is removed. As a result of the symmetric equipment, an angle of bending direction of 180° is possible without any necessary twisting of the wire. Besides during the bending of the wire it is considerably important that the heavy loading of housing 22 is reduced, so that the housing may be smaller, which increases the freedom of motion of the wire being bent. Bending with a much smaller radius is however harder to accomplish, since the distance of the wire axis from the hinges 88 and 90 need be reduced.

Figure 6:
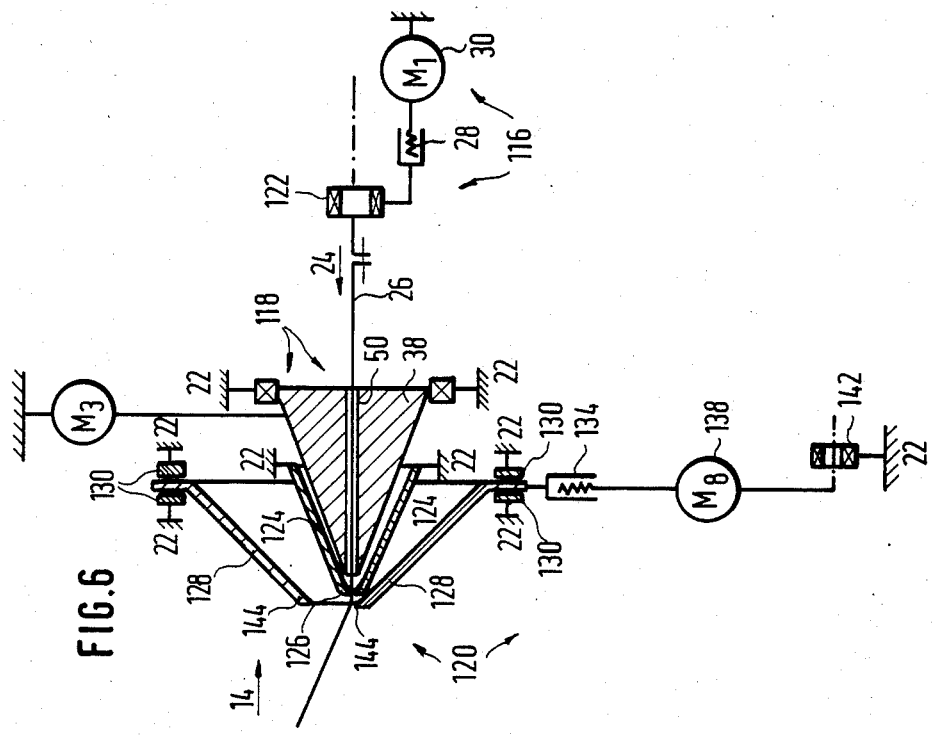
FIG. 6 is a view as in FIG. 1 of a further embodiment of the bending machine.
Figure 7:
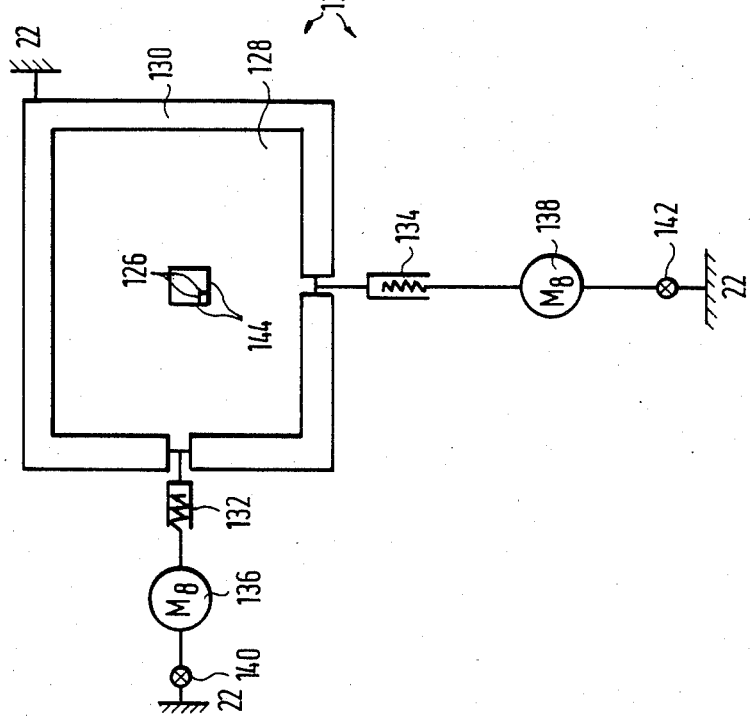
FIG. 7 is a front view of the bending machine of FIG. 6.

FIGS. 6 and 7 show a third embodiment of the bending machine which is designed for rectangular wire. To begin with it is herein already pointed out that this bending machine comes with four motors and that the effecting of the bending direction results not during twisting of the wire 26 but through changing the bending direction relative to the same machine.

The bending machine comprises further three main elements namely advancing apparatus 116, torsion apparatus 118 and bending apparatus 120. Subsequently now those parts of these main elements are explained, which are different from the first embodiment.

In the case of the advancing apparatus 116, the twisting of round wires by the previous wire rotation motor 32 of FIG. 1 is replaced by a bearing 122. This bearing transfers the advancing movement to the wire, so that the wire remains rotatable about its axis. With the torsion apparatus 118 the free rotatable lamination 40 is replaced by a fixed lamination 124. The lamination 124 is fixed to housing 22. Its shaping and its surface surrounding the wire 126 however corresponds to the rotatable lamination 40. The wire 26 is in this way simply movable in the direction of arrow 24 with the angular position of its axis remaining constant. Clearly this eliminates the necessity of a wire turning motor 48.

Similar to the embodiment of FIG. 1, the fixed lamination 124 of the yet to be explained embodiment serves furthermore as part of the bending apparatus 120. Further the bending apparatus 120 has a bending lamination 128, which is mounted above a movable frame 130 (FIG. 7) in the housing so that in a plane perpendicular to the wire axis (the plane of FIG. 7) all sides are movable. The exact position of the lamination 128 inside this plane is midway between two right angular to each other positioned screw drives 132 and 134, which are driven by motors 136 and 138. Both screw driving motors 136 and 138 are by bearings 140 and 142 fixed against the housing 22 and thereby also are movable at times in the moving direction of the other motors.

In the bending lamination 128 is a bending window 144 whose edge angle corresponds with the wire 26. The bending window 144 can thereby always contact the wire on two of its outer surfaces at the same time. Through corresponding dimensions of the window 144 however, it is assured that the wire has its remaining two sides freely movable.

The bending process takes place with the embodiment of FIGS. 6 and 7 in the following manner. The movement of the wire 26 takes place in the same manner as beforehand explained in FIG. 1. The wire 26 however then (FIG. 6) is twisted between the adjacent surface 50 of the torsion tool 38 and 126 of the fixed lamination 124. During the torsion process turning of the rearmost wire end will make a compensating turning by means of the bearing 122. Then the torsion movement by bending occurs between the surrounding surface 126 of the fixed lamination 124 and the bending window 144. In this way, the bending window 144 to begin with is usually so positioned that the wire on two side surfaces are in contact at the same time, and in the region of the bending direction, enough free room is left (in FIG. 7 toward the upper right). The exact bending direction is effected through the movement of both of the pushing motors 138 and 140 making relative movements between the bending lamination 128 and the bending window 144 and the adjoining wire surfaces 126 positioned on the fixed lamination 124. The absolute amount of the desired relative movement defines the size of the bending angle.

The embodiment of FIGS. 6 and 7 shows a simplified construction, nevertheless an especially stable mechanism is realized, with which the bending angle remains exactly determinable.

Clearly this invention can teach various modifications without departing from its scope. It has value especially in the shaping, the bearings and the drive elements for the single wire part. Furthermore, additional optical sensors or mechanical ones can be provided which improve the workmanship of the processed work by checking on the motor control computer. Furthermore the addition of common label markings and cutting apparatus is possible. With reference to the computers and the control programs it can be said, that now with known tools and known methods the programming may be realized. A detailed description of the computer and useful program would detract from the invention. Understandably it may be accomplished through the inside range of practical modifications of the control programs, for example of the possible use of word tables without substantial construction expense, with one and the same apparatus of the different benders and/or torsion processes. It is simply pointed out that for example in programs for and the practice of jaw orthopedics for temporary separations, the foregoing bending and torsion alterations can be adopted in such a way that after a known time the necessary rebending, for example, retwisting of the wire is decreased and the bending and twisting of a new wire automatically occurs namely without determination of new data by presentation of simply a part of the data.

We claim:

1. For use with orthodontic wire, a machine for filling prescriptions employing orthodontic wire by advancing, bending and twisting the wire comprising, wire advancing, bending and twisting means each of which are separately controlled by electronic commands to controlled stepping motors, said advancing means including a stepping motor drive for incrementally advaning a measured length of said wire along its axis to engage said wire after it passes through said bending and twisting means, said bending means including a movable bending edge movable substantially perpendicular to the axis of the wire by an associated drive means, said twisting means including two relatively opposing rotatable grippers having associated drive means for gripping two places axially spaced from one another on said wire, said gripping drive means comprising stepping drive motors for rotating said grippers relative to one another to twist said wire about its axis, a stepping motor coupled to said bending means for incrementally advancing the bending means against said wire to bend it away from its axis as it is held in said twisting means, and all of said stepping motors being programmable by counting a predetermined number of incremental step counts to advance bend and twist the wire to achieve desired wire patterns for filling orthodontic prescriptions.

2. The improved apparatus defined in claim 1 further comprising electronic computer means for controlling said stepping motors to advance and bend the wires in accordance with a prestored pattern stored in a computer to control the incremental steps for the stepping motors to advance and bend said orthodontic wire into the predetermined pattern of a prescription.

3. The improved apparatus defined in claim 2 further comprising said prestored prescription patterns for producing by the stepping motors the shape of dental wire pieces for use in the practice of orthondontics on the teeth and jaw of a particular patient.

* * * * *